United States Patent
Ptchelintsev

(10) Patent No.: US 7,842,316 B2
(45) Date of Patent: Nov. 30, 2010

(54) **COSMETIC COMPOSITIONS HAVING EXTRACTS OF *AMOMUM MELEGUETA* AND METHODS OF TREATING SKIN**

(75) Inventor: Dmitri Ptchelintsev, Jersey City, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 11/880,201

(22) Filed: Jul. 20, 2007

(65) Prior Publication Data

US 2007/0264364 A1  Nov. 15, 2007

(51) Int. Cl.
*A61K 36/00* (2006.01)

(52) U.S. Cl. .................. 424/725; 424/774; 424/775; 424/776; 424/777; 424/778

(58) Field of Classification Search .......... None
See application file for complete search history.

(56) References Cited

U.S. PATENT DOCUMENTS

| | | | |
|---|---|---|---|
| 5,053,222 A | 10/1991 | Takasu et al. | 514/106 |
| 5,879,682 A | 3/1999 | Allas et al. | 424/756 |
| 6,063,381 A | 5/2000 | Staggs | 424/734 |
| 6,071,541 A | 6/2000 | Murad | 424/616 |
| 6,217,852 B1 | 4/2001 | Gildenberg et al. | 424/59 |
| 6,593,371 B1 | 7/2003 | Staggs | 514/627 |
| 6,607,736 B2 | 8/2003 | Ohmori et al. | 424/401 |
| 2003/0152682 A1 | 8/2003 | Ley et al. | |
| 2004/0067245 A1 | 4/2004 | Mahalingam et al. | 424/401 |
| 2004/0175439 A1* | 9/2004 | Cyr | 424/725 |
| 2005/0058729 A1 | 3/2005 | Staggs | 424/734 |
| 2005/0095628 A1 | 5/2005 | Krempin et al. | 435/6 |
| 2005/0175718 A1* | 8/2005 | Menon et al. | 424/725 |
| 2005/0260290 A1 | 11/2005 | Raskin et al. | 424/756 |

FOREIGN PATENT DOCUMENTS

| | | |
|---|---|---|
| JP | 06239736 A | 8/1994 |
| WO | 98/47482 A | 10/1998 |

OTHER PUBLICATIONS

Duke, J. Handbook of Medicinal Herbs. 2nd ed. 2002. CRC Press, NY, NY, p. 346.*
Manual for the Propagation and Cultivation of Medicinal Plants of Ghana. 2002. Aburi Botanic Garden. pp. 4-32.
Igwilo et al. Int. J. Pharmacognosy. 1991. vol. 29, No. 1, pp. 45-50, BIOSIS Abstract enclosed.
Enyikwola, O. Int. J. Pharmacognosy. 1994. vol. 32, No. 1, pp. 37-43, BIOSIS Abstract enclosed.
Umukoro S. et al, "Effect of *Aframomum meleguta* seed extract on thermal pain and carrageenin—induced oedema" Nigerian Quarterly Journal of Hospital Medicine, Lagos Univ Medical Soc, Lagos, NG vol. 11, No. 1-04, Dec. 1, 2001.
Duke, J.A. et al. "CRC Handbook of Medicinal Spices" 2002, CRC Press URL:http://books.google.de/books?id=g_OC16POvsYC &printsec=frontcover&dqCRC+handbook+of+medicinal+spices.

* cited by examiner

*Primary Examiner*—Christopher R. Tate
(74) *Attorney, Agent, or Firm*—Joan M. McGillycuddy; Charles J. Zeller; Anthony M. Santini

(57) ABSTRACT

There is disclosed a topical composition and method for preventing and/or ameliorating the effects of aging on skin to improve the aesthetic appearance of skin and/or scalp. The invention utilizes the topical application of *Amomum melegueta* extract.

13 Claims, No Drawings

COSMETIC COMPOSITIONS HAVING EXTRACTS OF *AMOMUM MELEGUETA* AND METHODS OF TREATING SKIN

BACKGROUND OF THE INVENTION

1. Field of the Invention

The present invention relates to compositions that improve the aesthetic appearance of skin. More particularly, the present invention relates to topical cosmetic compositions having extracts of *Amomum melegueta* to treat aging skin.

2. Description of the Related Art

The appearance and physical properties of human skin cells, especially keratinocytes, fibroblasts and sebocytes, change with age. In particular, the ability of these cells to transport in and utilize glucose decreases.

A loss in take up and utilization of glucose manifests in an increased concentration of glucose in the extra cellular matrix and a decrease in cell metabolism. Decreased cell metabolism reduces both cell replication and cell vitality. For example, a reduction in the rate of replication of basal epidermal cells reduces the thickness of the epidermis and, thus, the skin. In addition, increased extra cellular glucose accumulation in the skin leads to what is known as the formation of Advanced Glycation End (AGE) products and the loss of functional properties of collagen and elastin. Moreover, key inflammatory mediators such as cyclooxygenase-2 (COX-2) enzyme and tumor necrosis factor (TNF)-alpha enzyme are believed to be responsible for both acute skin inflammation and sub-acute chronic inflammation, the cumulative degenerative effects of which lead to intrinsic and extrinsic aging. Thus, wrinkles, sallowness and a decrease in the mechanical properties and the overall aesthetic appearance of the skin occurs over time.

SUMMARY OF THE INVENTION

It is an object of the present invention to provide one or more topical compositions and methods of use to improve the aesthetic appearance of skin.

It is also an object of the present invention to provide one or more topical compositions and methods of use to prevent and/or ameliorate the effects of extrinsic and/or intrinsic aging on the skin.

It is another object of the present invention to provide one or more topical compositions and methods of use to prevent and/or reduce wrinkling of the skin.

It is still another object of the present invention to provide one or more topical compositions and methods of use to prevent and/or reduce sagging of the skin.

These and other objects and advantages of the present invention are achieved by one or more topical compositions that have an effective amount of an extract of *Amomum melegueta* and optionally a cosmetically acceptable vehicle.

DETAILED DESCRIPTION OF THE INVENTION

The present invention has unexpectedly and surprisingly found that a topical composition can be formulated to improve the aesthetic appearance of skin (including lips), particularly to prevent and/or ameliorate the effects of extrinsic and/or intrinsic aging of the skin. Intrinsic aging may include chronological aging. Extrinsic aging may include photoaging from ultraviolet light exposure and the effects of environmental pollution. The effects of skin aging include, but are not limited to: fragile skin, sagging skin, fine lines and/or wrinkles, thinning skin, lack-luster skin, fatigued skin, and dry skin. The present invention also provides a warming effect on skin.

The topical composition has an effective amount of an extract of *Amomum melegueta*. The *Amomum melegueta* extract can be applied to the skin and/or scalp for a period of time and in an amount sufficient to prevent and/or ameliorate the skin condition. The extract can be applied as a composition of a pure extract or in a cosmetically acceptable vehicle.

*Amomum melegueta* extract is obtained from the Amomum melegueta plant. *Amomum melegueta* plant is also known by the name of Grains of Paradise. Any part of the plant, such as the roots, can be used to obtain the extract. Over-the-ground parts, such as the leaf, stem, seeds, bark, fruit and flower are preferred. Seeds are most preferred.

The extract may be obtained by any known extraction process with any known extraction solvent. The process can include one or more extractions with one or more solvents or mixtures of solvents. Useful extraction solvents include hydrophilic and hydrophobic solvents and any mixtures thereof. Supercritical fluids are also useful extraction solvents. If desired, solvents can be evaporated after extraction, and resulting residues can be used as is or be freeze-dried or reconstituted in another solvent(s) or mixture thereof in which the extract is either soluble, dispersible or suspendable. Examples of hydrophilic solvents include water, methanol, ethanol, brine solution, and solutions of solvent with inorganic and organic salts. Examples of hydrophobic solvents include liquid hydrocarbons, such as butane, pentane, hexane, heptane, and octane, as well as other water-immiscible organic compounds, such as ether, ester, amide, ketone, and aldehyde. Most preferred water-immiscible/hydrophobic solvents include hexane, diethyl ether, octanol, hexanol, and heptanol.

The extract can also be extracted with organic solvents that are partially water miscible and/or completely water miscible. Examples of such solvents include ethyl acetate; methyl acetate; lower ketones having no more than 4 carbon atoms, such as acetone; lower aldehydes having no more than 3 carbons, such as formaldehyde and acetaldehyde; and lower acid anhydrides, such as acetic acid anhydrides. An example of a useful supercritical solvent is liquid carbon dioxide.

The effective amount of *Amomum melegueta* extract and the duration of its application will vary with the particular condition being treated, the age and physical condition of the person, the severity of the condition, the nature of concurrent therapy, the particular topical vehicle utilized, and like factors in the knowledge and expertise of those skilled in the art. The duration of application may be once or twice a day for a period of at least one week, two weeks or more.

Compositions of the present invention may take the form of a pure extract or an extract in combination with a cosmetically acceptable vehicle and/or additional ingredients. Preferably, *Amomum melegueta* extract is present from about 0.0001 weight percent (wt %) to about 90 wt % based on the total weight of the composition. More preferably, the extract is present from about 0.001 wt % to about 50 wt %. Most preferably, the extract is present from about 0.01 wt % to about 15 wt %. The above amounts are based on "active amount" of *Amomum melegueta* extract absent diluent, solvent, or any other ingredient added for bulk. In addition, all weight percentages disclosed herein are based on the total weight of the composition unless otherwise noted.

The present invention preferably includes a cosmetic vehicle. Such vehicles may take the form of any known in the art suitable for application to skin or scalp. These vehicles may include water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing. Additional ingredients that may be included in the vehicle are disclosed in U.S. Pat. No. 5,162,378 (column 4, et seq.), which additional ingredients are incorporated herein by reference. Preferred vehicles include one or more silicone oils.

Preferred compositions have about 0.01 wt % to about 60 wt % of the vehicle based on the total weight of the composition. More preferred compositions have about 1 wt % to about 30 wt % of the vehicle. Most preferred compositions have about 2 wt % to about 20 wt % of the vehicle.

The present composition can be made into any suitable product form, such as aerosol, cake, cream, ointment, emulsion, essence, foam, gel, lotion, mousse, paste, patch, pencil, serum, solution, towelette, mask, body wrap, spray and stick. If desired, the composition can also be formulated into make-up cosmetics, shampoos and conditioners.

The composition may also have one or more of the following optional additional ingredients: anesthetics; anti-allergenic; antimicrobials; antifungals; anti-inflammatories; antiseptics; chelating agents; colorants; depigmenting agents; emollients, such as dimethicone, polysilicones and cyclomethicone; exfollients, such as retinal, retinol and retinoic acid; fragrances; emulsifiers; humectants; insect repellents; lubricants; moisturizers; pharmaceutical agents; preservatives; skin penetration enhancers; skin protectants; stabilizers; sunscreens; surfactants; thickeners; viscosity modifiers; and vitamins.

Particularly useful additional ingredients are vitamins. The extract can be combined with vitamins such as vitamin A, vitamins of the B group, vitamin C, vitamin E, and derivatives thereof. Useful derivatives include retinal, retinol, retinoic acid, and other related compounds having retinoid or retinoid-like activity, magnesium ascorbyl phosphate, sodium ascorbyl phosphate, tocopheryl ascorbyl phosphate, and ascorbyl tocopheryl maleate. Preferred compositions have about 0.001 wt % to about 50 wt % vitamins based on the total weight of the composition. More preferred compositions have about 0.025 wt % to about 25 wt % vitamins. Most preferred compositions have about 0.025 wt % to about 25 wt % vitamins.

Other particularly useful additional ingredients are sunscreens. Preferred sunscreens are those with a broad range of UVB and UVA protection, such as octocrylene, avobenzone (Parsol 1789), octyl methoxycinnamate, homosylate, benzophenone, camphor derivatives, zinc oxide, and titanium dioxide. Preferred compositions have about 0.01 wt % to about 70 wt % sunscreens based on the total weight of the composition. More preferred compositions have about 0.1 wt % to about 60 wt % sunscreens. Most preferred compositions have about 1 wt % to about 45 wt % sunscreens.

Other particularly useful additional ingredients are exfoliating agents, such as alphahydroxyacids, betahydroxyacids, oxa acids, oxa diacids, and their derivatives such as esters, anhydrides and salts thereof. A most preferred exfoliating agent is glycolic acid. Preferred compositions have about 0.1 wt % to about 80 wt % exfoliating agents based on the total weight of the composition. More preferred compositions have about 1 wt % to about 40 wt % exfoliating agents. Most preferred compositions have about 1 wt % to about 15 wt % exfoliating agents.

Other particularly useful additional ingredients are anti-inflammatories. The anti-inflammatories may be of synthetic, natural or semi-synthetic origin. The anti-inflammatories may be steroidal or non-steroidal. Useful examples include, but are not limited to, mangostin, eysenhardtia polistachya (Palo Azul) wood extract, rosemary extract, camphor, salicylates, hydrocortisone, aspirin, indomethacin, mefenamic acid and derivatives thereof. Preferred compositions have about 0.01 wt % to about 25 wt % anti-inflammatories based on the total weight of the composition. More preferred compositions have about 0.1 wt % to about 15 wt % anti-inflammatories. Most preferred compositions have about 0.5 wt % to about 10 wt % anti-inflammatories.

The compositions of the present invention may be topically applied to the skin and/or scalp to reduce the extrinsic and/or intrinsic aging on and to enhance to the aesthetic appearance of the skin and/or scalp, as well as to provide a warming effect on the skin and/or scalp.

The effects of skin aging include, for example, fragile skin, sagging skin, fine lines and/or wrinkles, thinning skin, lackluster skin, fatigued skin, dry skin, skin irritation, skin sensitivity, dark eye circles, puffy skin around eyes, irregular skin pigmentation, and melasma.

Topically applying compositions of the present invention to the skin can enhance and improve the aesthetic appearance of skin by, among other improvements, reducing skin irritation, decreasing skin fragility; preventing and reversing deterioration of collagen and/or elastin; preventing skin atrophy; promoting/accelerating cell turnover; improving skin firmness/plumpness; improving skin texture; decreasing fine lines and wrinkles; improving skin tone; enhancing skin thickness; restoring skin luster; minimizing signs of fatigue; reducing skin dryness; reducing skin itchiness; reducing skin redness; reducing sensitivity to chemical, mechanical or radiation impact; reducing propensity of the skin to flush and blush; reducing dark circles and puffiness in the periorbital eye area; reducing frown lines on the forehead and laugh lines around the mouth; increasing cell proliferation; decreasing the extent and/or duration of bruising visible after physical trauma; reducing blotchiness and irregular skin pigmentation; treating or ameliorating melasma; treating or ameliorating skin hyperpigmentation; treating or ameliorating foliculitis barbae and ingrown hair bumps and after-shave nicks and irritation; treating or ameliorating dermatitis, psoriasis and other skin conditions affiliated with or caused by acute, subacute or subchronic inflammation; and enhancing overall skin health.

EXAMPLES

Example I

COX-2 Inhibition Activity

*Amomum melegueta* extract was suspended in 95% ethanol to appropriate concentration prior to in vitro assays. The calorimetric COX (ovine) inhibitor screening assay was used to test the COX-2 inhibitory activity of the *Amomum melegueta* extract. This assay uses the peroxidase component cyclooxygenase to measure the peroxidase activity calorimetrically by monitoring appearance of oxidized colorimetric substrate. The enzyme was added in the wells of a plate followed by the ethanolic solution of calorimetric substrate.

The reagents were carefully mixed by shaking the plate. The calorimetric substrate solution was added to the wells followed by addition of COX-2 substrate, arachidonic acid. The plate was again carefully shaken. Inhibitory activity was calculated from these absorbance readings. Commercial drug and COX-2 inhibitor, Vioxx (Merck, Inc.), was used as a positive control.

At the concentration of 1 mg/ml, the *Amomum melegueta* extract demonstrated high inhibitory activity against the enzyme similar to the commercial drug Vioxx (Merck, Inc.) used as a control. The level of inhibition for the *Amomum melegueta* extract was 92% compared to 90% for Vioxx.

Example II

TNF-alpha Inhibition Activity

To test the efficacy of *Amomum melegueta* extract for the inhibition of TNF-alpha production, an enzyme linked immunoassay (ELISA) commercially available from R&D Systems was employed.

This assay employed the quantitative sandwich enzyme immunoassay technique in which a monoclonal antibody specific for TNF-alpha has been pre-coated onto a microtiter plate. Culture supernatants from cells exposed to the active material were pipetted into separate wells. TNF-alpha in the supernatant was bound to the plate via the immobilized antibody. After several washes to remove unbound antibody, an enzyme-linked polyclonal antibody specific for TNF-alpha was added to each well. Following a wash to remove unbound antibody-enzyme reagent, a substrate solution was added to the wells. Color develops in proportion to the amount of TNF-alpha bound in the initial step. The results of the tests showed that the Amomum melegueta extract provided a 60 to 90% degree of TNF-alpha inhibition.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method of improving the aesthetic appearance of aging-related wrinkled skin comprising topically applying to the aging-related wrinkled skin of a subject in need thereof a composition consisting essentially of an *Amomum melegueta* extract, and optionally a cosmetically acceptable vehicle, in an amount effective for improving the aesthetic appearance of the wrinkled skin.

2. The method of claim 1, wherein the extract is applied in an amount from about 0.0001 wt. % to about 90 wt. % based on the total weight of the composition.

3. The method of claim 1, wherein the extract is applied in an amount from about 0.001 wt. % to about 50 wt. % based on the total weight of the composition.

4. The method of claim 1, wherein the extract is applied in an amount from about 0.01 wt. % to about 15 wt. % based on the total, weight of the composition.

5. The method of claim 1, wherein the extract is obtained from a part selected from the group consisting of leaf, stem, seeds, bark, fruit and flower of the *Amomum meleguela* plant.

6. The method of claim 1, wherein the extract is obtained from seed of the *Amomum meleguela* plant.

7. The method of claim 1, wherein the composition is applied for a period of time sufficient to improve the aesthetic appearance of the aging-related wrinkled skin.

8. The method of claim 1, wherein the composition is applied at least once daily for at least one week.

9. The method of claim 1, wherein the composition is applied to the aging-related wrinkled skin of said subject for a period of time sufficient to and/or ameliorate the effects of extrinsic and/or intrinsic aging of skin.

10. The method of claim 9, wherein the intrinsic aging comprises chronological aging.

11. The method of claim 9, wherein the extrinsic aging is selected from the group consisting of photoaging, the effects of pollution, the effects of other environmental stressors, and any combinations thereof.

12. The method according to claim 1, wherein the composition is applied to the aging-related wrinkled skin of said subject thereby inhibiting COX-2 enzyme and/or TNF-alpha enzyme.

13. The method according to claim 1, wherein the composition is in the form of in a cream, an emulsion, a gel, a mousse, a lotion, a paste, a serum, a mask, or a body wrap product.

* * * * *